United States Patent [19]

Koishikawa et al.

[11] Patent Number: 5,445,548

[45] Date of Patent: Aug. 29, 1995

[54] EXHAUST GAS SAMPLING DEVICE FOR OUTBOARD MOTOR

[75] Inventors: Koji Koishikawa; Motoyoshi Shishido, both of Wako, Japan

[73] Assignee: Honda Giken Kogyo Kabushiki Kaisha, Tokyo, Japan

[21] Appl. No.: 306,495

[22] Filed: Sep. 15, 1994

[30] Foreign Application Priority Data

Sep. 16, 1993 [JP] Japan .................. 5-229940

[51] Int. Cl.⁶ ............................. B63H 21/32
[52] U.S. Cl. ..................... 440/89; 73/23.31; 123/703
[58] Field of Search .......... 440/89; 123/572; 73/29.31, 29.32, 863.42

[56] References Cited

U.S. PATENT DOCUMENTS

| | | | |
|---|---|---|---|
| 4,903,648 | 2/1990 | Lassankse | 123/703 |
| 5,383,440 | 1/1995 | Koisikawa et al. | 123/572 |

FOREIGN PATENT DOCUMENTS 4-121296  4/1992  Japan .

*Primary Examiner*—Jesus D. Sotelo
*Attorney, Agent, or Firm*—Armstrong, Westerman, Hattori, McLeland & Naughton

[57] ABSTRACT

In an outboard motor, an exhaust pipe coupled to a lower surface of a cylinder head of an engine extends downwardly through an oil case. An exhaust port, defined at a lower end of the exhaust pipe, is opened downwardly into an extension case. An exhaust gas sampling pipe, threadedly inserted into a seat surface formed on a lower surface of the extension case, extends upwardly into the exhaust pipe and has its inner end inserted into the exhaust port in the exhaust pipe. An outer end of the exhaust gas sampling pipe, extending out of the extension case, is closed by a detachable cap. Thus, it is easy to mount the exhaust gas sampling pipe for sampling an exhaust gas from the exhaust pipe for the outboard motor.

1 Claim, 6 Drawing Sheets

EXHAUST GAS SAMPLING DEVICE FOR OUTBOARD MOTOR

BACKGROUND OF THE INVENTION

1. Field of the Invention

The present invention relates to an exhaust gas sampling device for an outboard motor, designed to sample an exhaust gas from an engine through an exhaust gas sampling pipe.

2. Description of the Prior Art

Recently, in order to protect lake water from being stagnated or polluted, due to the exhaust gas discharged from an engine of an outboard motor, we are required to analyze harmful components contained in such exhaust gas.

Some exhaust gas sampling devices, for sampling exhaust gas through an exhaust gas sampling pipe provided in an exhaust gas passage, have been proposed (for example, see Japanese Patent Application Laid-open No. 121296/92).

The above prior art exhaust gas sampling device is mounted in the intermediate portion of an exhaust pipe. The exhaust gas sampling pipe extends horizontally through a wall of the exhaust pipe and through an extension case to the outside of the outboard motor. Thus, the exhaust gas can be sampled without removal of a cover for the outboard motor.

However, the prior art exhaust gas sampling device suffers from a problem that, if the exhaust gas sampling pipe is intended to be disposed to extend through both of the exhaust pipe and the extension case, as described above, openings in the exhaust pipe and extension case may not be aligned with each other, resulting in difficulty in mounting the exhaust gas sampling pipe.

SUMMARY OF THE INVENTION

Accordingly, it is an object of the present invention to provide an exhaust gas sampling device for an outboard motor, wherein an exhaust gas sampling pipe can easily be mounted.

To achieve the above object, according to the present invention, there is provided an exhaust gas sampling device for an outboard motor comprising an engine, a body case, which rotatably supports a propeller driven by the engine and which defines an exhaust gas passage for permitting an exhaust gas from the engine to be passed therethrough into water, an exhaust pipe, having an exhaust port opened downwardly into the body case, an exhaust gas sampling pipe, extending through the body case, and a cap for closing an outer end of the exhaust gas sampling pipe, wherein an outer wall surface of the body case, opposed to the exhaust port in the exhaust pipe, is provided with a seat, and an inner end of the exhaust gas sampling pipe, mounted to the seat, is loosely fitted into the exhaust port in the exhaust pipe from below.

With the above construction, because the inner end of the exhaust gas sampling pipe, mounted to the seat formed on the body case of the outboard motor, is loosely fitted into the exhaust port, in the exhaust pipe opened and downwardly into the body case, the need for accurately positioning the exhaust gas sampling pipe with respect to the exhaust pipe, when mounting the sampling pipe to the body case, is eliminated and leads to an improved assembling workability. Moreover, the exhaust gas sampling pipe is not in direct contact with the exhaust pipe and therefore, vibration of the engine is not transmitted through the exhaust pipe to the exhaust gas sampling pipe which leads to an improved durability of the exhaust gas sampling pipe and also eliminates sealing of the connection between the exhaust gas sampling pipe and the exhaust pipe.

The above and other objects, features and advantages of the invention will be apparent from the following description of preferred embodiments taken in conjunction with the accompanying drawings.

BRIEF DESCRIPTION OF THE DRAWINGS

FIGS. 1 to 5 illustrate a first embodiment of the present invention, wherein

FIG. 1 is a side view of the outboard motor;

FIG. 2 is an enlarged sectional view of essential portions of the motor shown in FIG. 1;

FIG. 3 is a view taken along line 3—3 in FIG. 2;

FIG. 4 is an enlarged sectional view taken along line 4—4 in FIG. 2;

FIG. 5 is an enlarged view of a portion indicated at 5, FIG. 4; and

DESCRIPTION OF THE PREFERRED EMBODIMENTS

The present invention will now be described by way of preferred embodiments in connection with the accompanying drawings.

Figure 1:
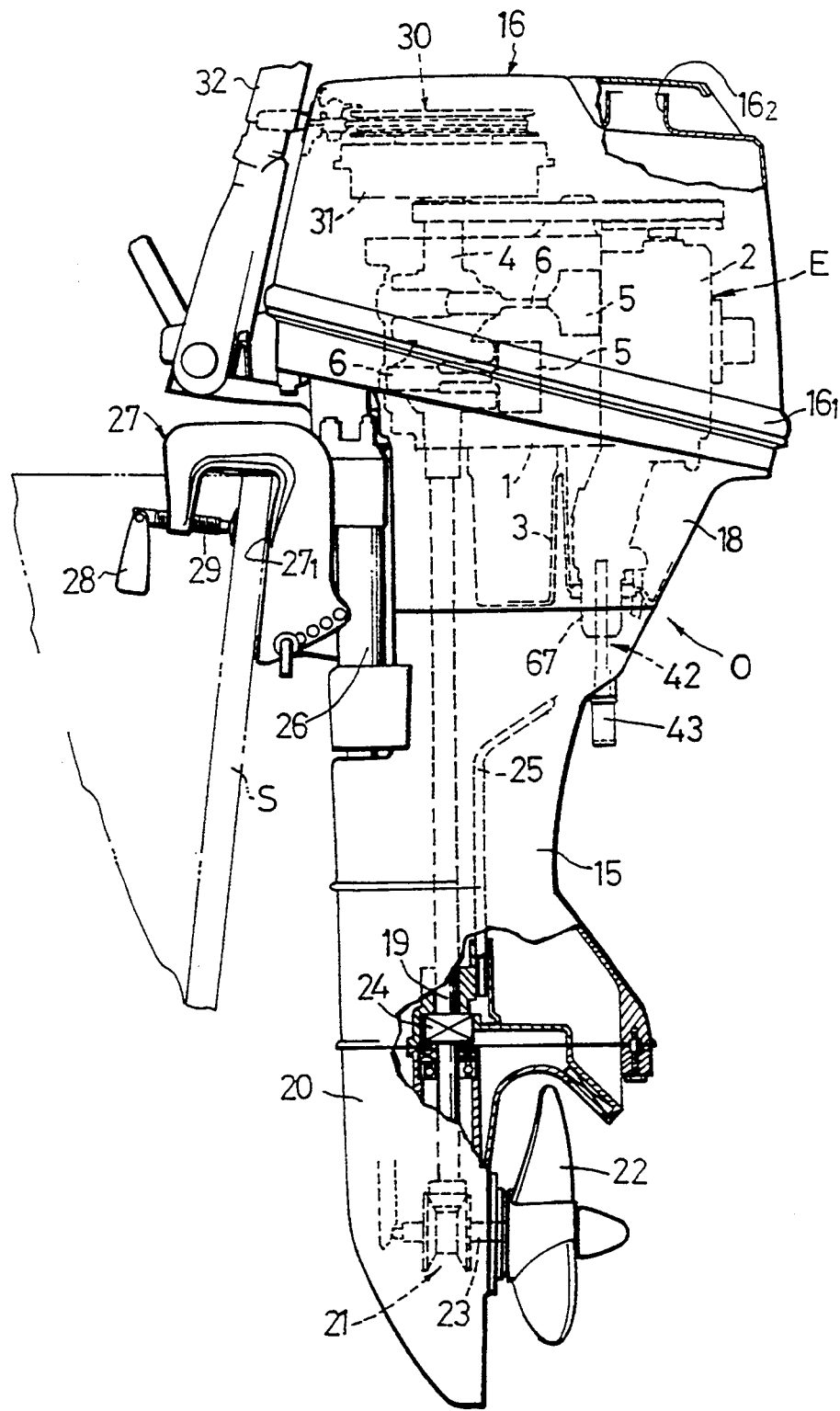
Figure 2:
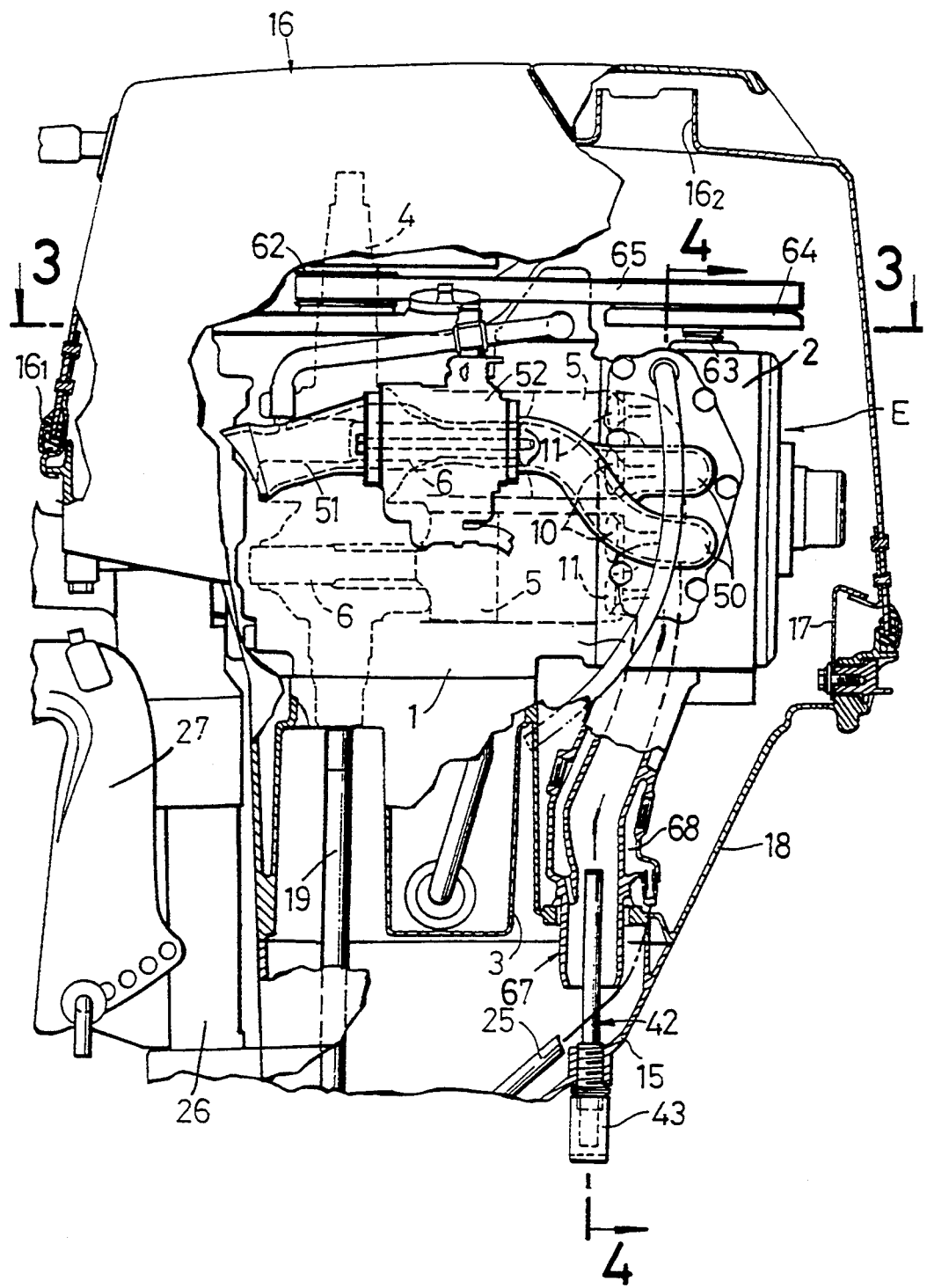
Figure 3:
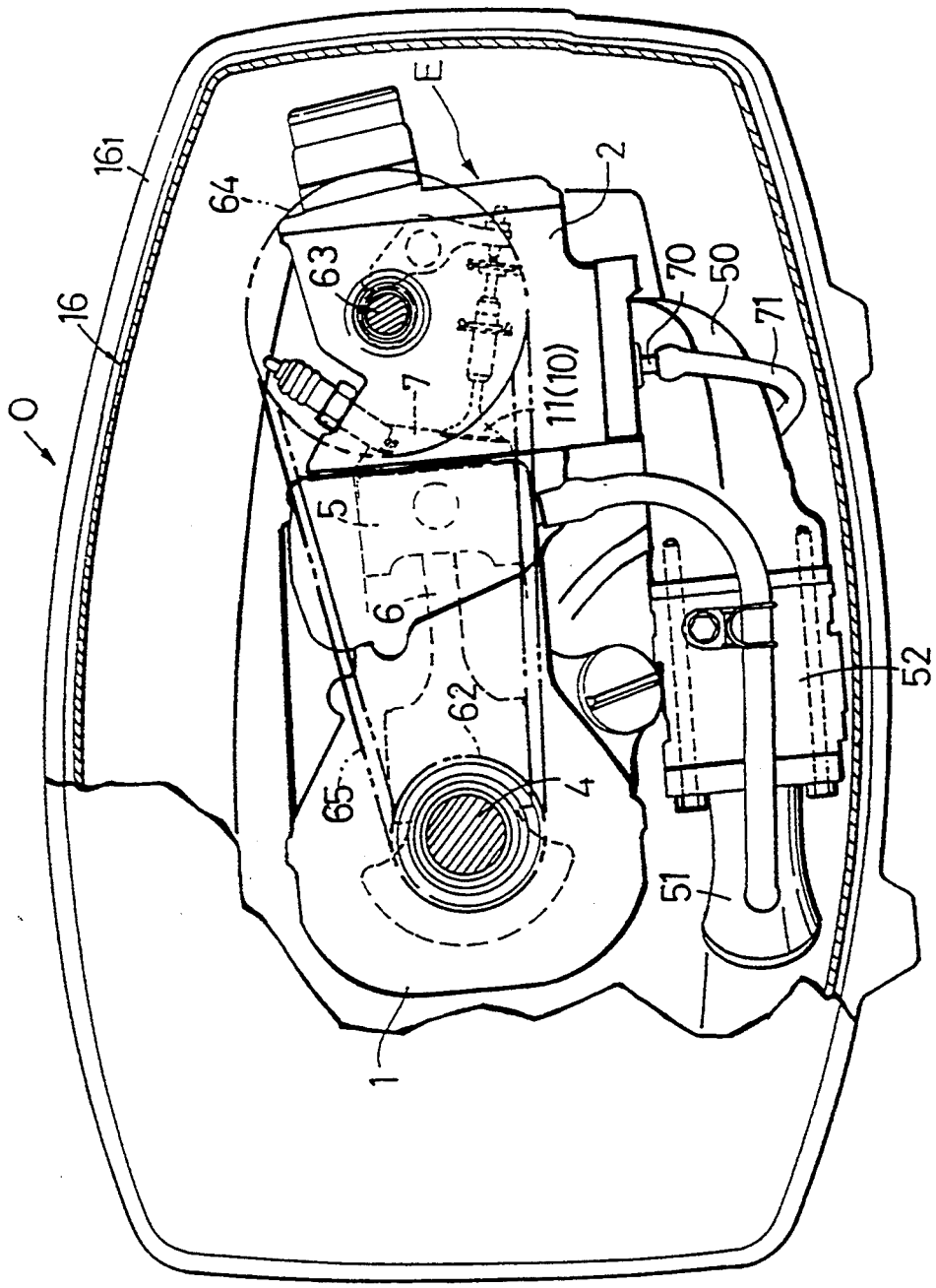
Figure 4:
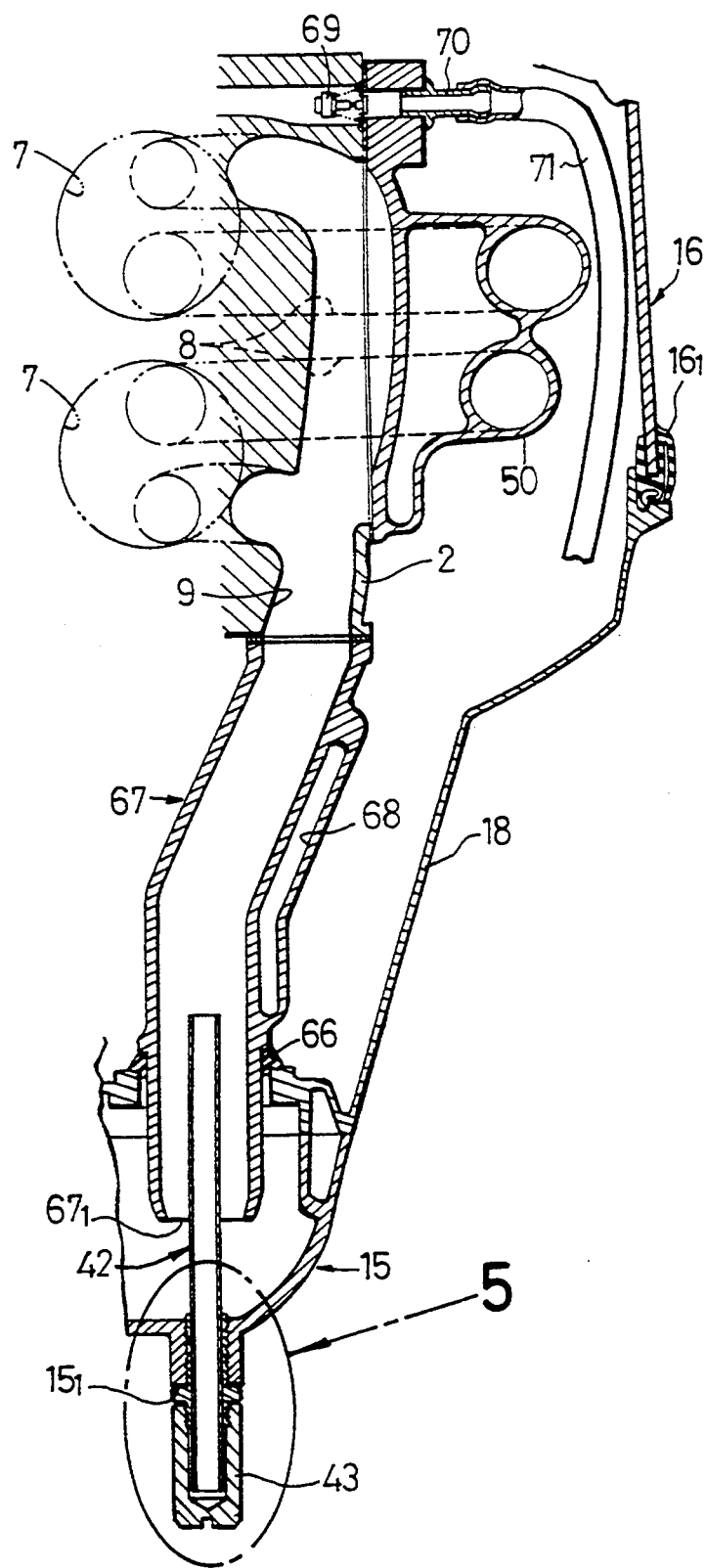

Referring to FIGS. 1 to 3, a 2-cylinder vertical engine E is mounted on an upper portion of an outboard motor 0 and includes an engine block 1 and a cylinder head 2 integrally coupled to each other. A crankshaft 4, supported vertically in the engine block 1, is connected with pistons 5, 5, supported horizontally in the engine block 1, through connecting rods 6, 6. Intake ports 8, 8 and exhaust ports 9, 9, FIG. 4, are defined in the cylinder head 2 and connected to combustion chambers 7, 7. Intake valves 10, 10 and exhaust valves 11, 11, FIG. 2 are mounted in the intake ports 8, 8 and the exhaust ports 9, 9, respectively, and opened and closed by a cam shaft 63. The cam shaft 63 is connected through a timing belt 65 and a follower pulley 64 to a driving pulley 62 mounted on the crankshaft 4. A carburetor 52 and an air intake 51 are connected to a front end of an intake pipe 50, extending from a left side of the cylinder head 2, FIG. 2, forwardly of the outboard motor 0.

An oil pan 3 is integrally formed within an oil case 18 interposed between an extension case 15 and the engine block 1. An engine cover 16 is detachably coupled to an opening at an upper end of the oil case 18. The oil case 18 and the engine cover 16 are separatably coupled to each other through a bracket 17 extending downwardly from the engine cover 16. A sealing member $16_1$, FIG. 1, is mounted around an outer periphery of the engine cover 16 for sealing a junction of the engine cover 16 with the oil case 18.

A driving shaft 19 is connected in series to a lower end of the crankshaft 4 of the engine E, and extends downwardly within the extension case 15. The driving shaft 19 is connected, at its lower end, to a propeller shaft 23. The propeller shaft 23 includes a propeller 22 connected, at its rear end, to shaft 19 through a bevel gear mechanism 21 mounted within a gear case 20. Thus, cooling water, pumped by a cooling water pump 24, mounted at a lower portion of the driving shaft 19, is supplied to the engine via a cooling water pipe 25. The extension case 15 and the gear case 20 constitute a body case of the present invention.

A stern bracket 27, for steerably supporting the outboard motor 0 through a swivel case 26, is fixed, by a set screw 29, operated by a lever 28, in a state where a groove $27_1$, opened at its lower end, is engaged with a stern S.

In FIG. 1, reference character 30 is a recoil starter; reference character 31 is a flywheel mounted at an upper end of the crankshaft 4; reference character 32 is a steering handle; and reference character 162 is an air intake port provided in the engine cover 16 to introduce the open air into an engine room.

As is apparent from FIG. 4, together with FIGS. 1 to 3, an exhaust pipe 67 passes through the oil case 18, via sealing member 66 and is coupled to a lower surface of the cylinder head 2. An exhaust port $67_1$ is made at a lower end of the exhaust pipe 67 and opened downwardly within the extension case 15. The cooling water pipe 25, FIG. 1 extending upwardly from the cooling water pump 24, is connected to a lower end of a water jacket 68, FIG. 2. The water jacket 68 is defined around an outer periphery of the exhaust pipe 67. The water jacket 68 is connected, at its upper end, to a lower end of another water jacket (not shown) defined in the cylinder head 2 and the engine block 1. The water jacket in the cylinder head 2, FIG. 3, is connected, at its upper end, to a drainage pipe 71 through a thermostat 69, FIG. 4, and a joint 70 mounted in an outer wall of the intake pipe 50. The drainage pipe 71 extends downwardly and is opened into an internal space in the extension in the extension case 15.

Figure 5:
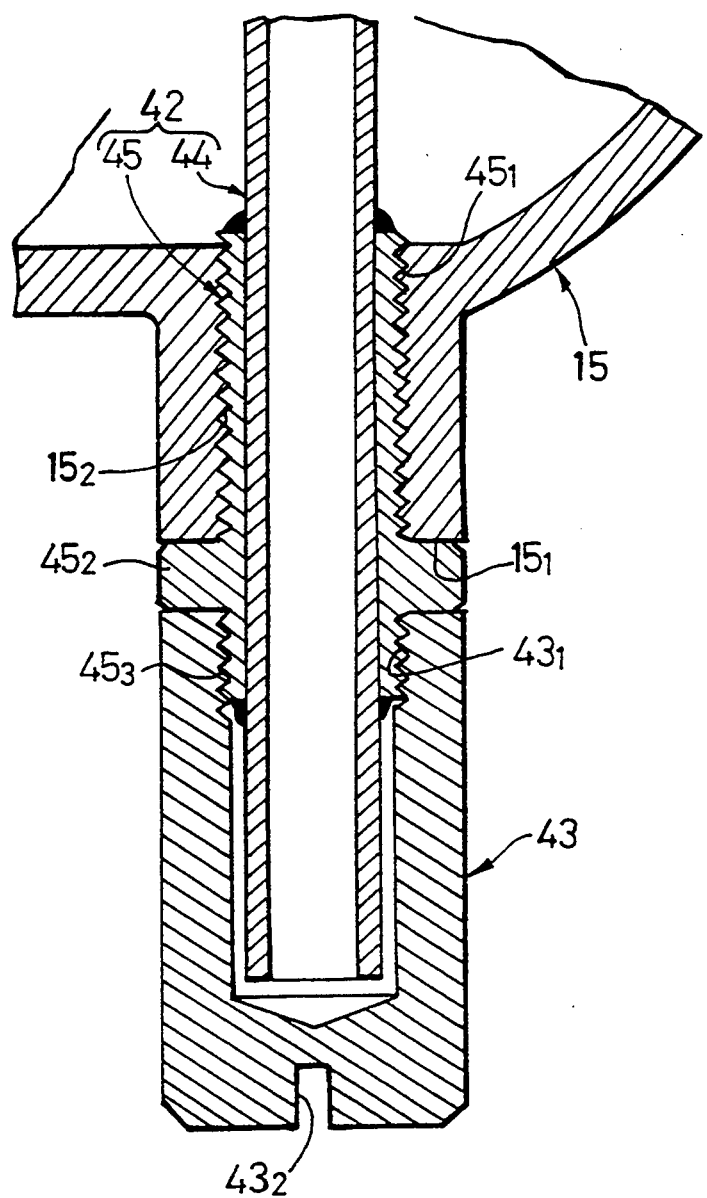

As can be seen from FIG. 5, a flat seat surface $15_1$ is formed on an outer wall surface of the extension case 15, opposed to the exhaust port $67_1$, FIG. 4, provided at the lower end of the exhaust pipe 67. An exhaust gas sampling pipe 42, FIGS. 4 and 5, is threadedly inserted into the seat surface $15_1$. The exhaust gas sampling pipe 42 includes a straight pipe member 44 and a cylindrical screw member 45 fitted over and integrally welded to the straight pipe member 44. The screw member 45 is provided at its outer periphery with a first external threaded portion $45_1$, a flange portion $45_2$ and a second external threaded portion $45_3$. The first external threaded portion $45_1$ is threadedly inserted into an internal threaded portion $15_2$ of the extension case 15, and the flange portion $45_2$ is brought into close contact with the seat surface $15_1$ of the extension case 15. An inner end of the pipe member 44, extending upwardly, is inserted into the exhaust port $67_1$ and opened into the exhaust pipe 67, FIG. 4.

An outer end of the pipe member 44 of the exhaust gas sampling pipe 42 extends to the outside of the extension case 15. A cap 43, FIG. 5, having an internal threaded portion $43_1$ threadedly engaged with the second threaded portion $45_3$ of the screw member 45, is put into abutment against the flange portion $45_2$ of the screw member 45, whereby the outer end of the pipe member 44 is closed to prevent an exhaust gas from being leaked. The cap 43 is provided with a screwdriver groove $43_2$ into which a tip end of a screw-drive can be engaged.

When the components of an exhaust gas are to be measured, the tip end of the screw-driver is engaged into the groove $43_2$ in the cap 43 to unscrew the cap 43, thereby removing the cap 43 from the gas exhaust gas sampling pipe 42. A tube, connected to an exhaust gas component measuring apparatus, not shown, is connected to the outer end of the pipe member 44 of the exposed exhaust gas sampling pipe 43. If the engine E is operated in this condition, the inside of the exhaust pipe 67 is filled up with an exhaust gas, so that a fresh exhaust gas can be sampled through the exhaust gas sampling pipe 42 inserted into the exhaust pipe 67.

When mounting the exhaust gas sampling pipe 42 to the outboard motor 0, as described above, the only thing which is necessary is to threadedly insert the exhaust gas sampling pipe 42 into the seat surface $15_1$, FIG. 5, of the extension case 15 from the outside. It is unnecessary to accurately align the exhaust gas sampling pipe 42 relative to the exhaust pipe 67. Therefore, the assembling workability is substantially impaired. In addition, the exhaust gas sampling pipe 42 is not in contact with the exhaust pipe 67 and vibration of the engine E is not transmitted directly to sampling pipe 42. Therefor, it is possible, not only to prevent a damage to the exhaust gas sampling pipe 42 due to the vibration, but also to eliminate the need for sealing a connection between the exhaust gas sampling pipe 42 and the exhaust pipe 67.

Figure 6:
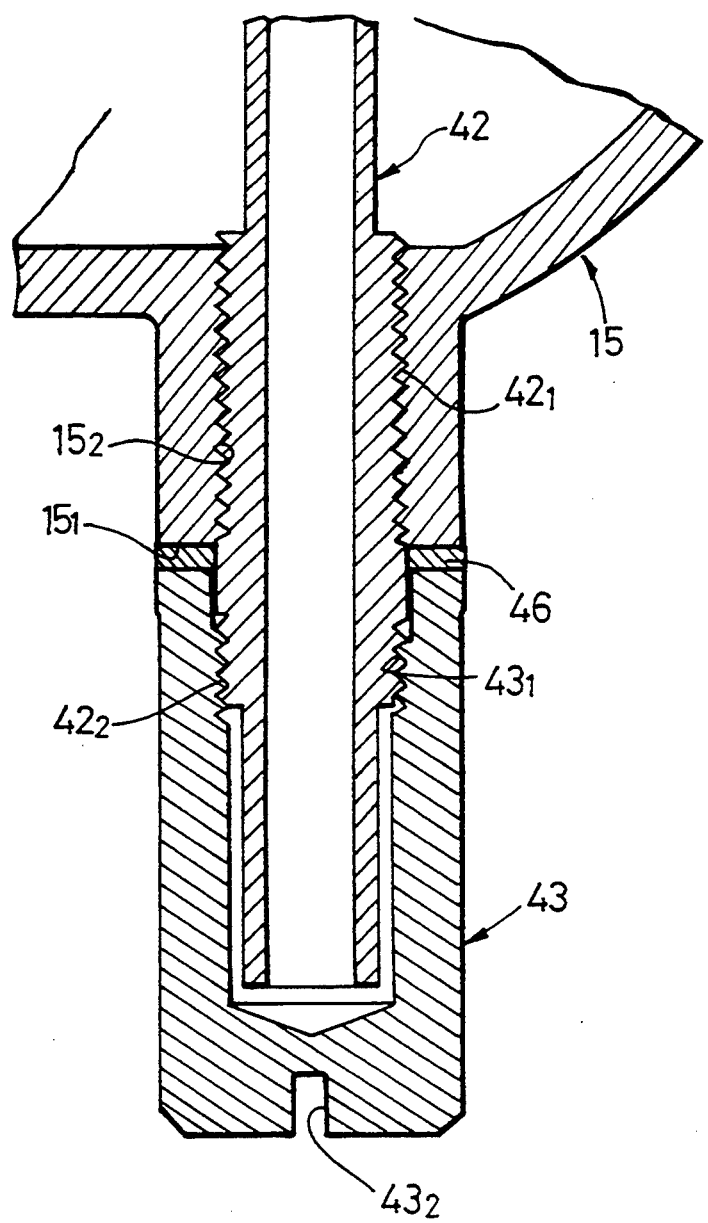
FIG. 6 is a view similar to FIG. 5, but illustrating an exhaust gas sampling pipe according to a second embodiment of the present invention.

FIG. 6 illustrates a second embodiment of an exhaust gas sampling pipe 42.

this exhaust gas sampling pipe 42, FIG. 6, includes a stud pipe having a first external threaded portion $42_1$ and a second external threaded portion $42_2$, both integrally provided around an outer periphery of the pipe 42. The first external threaded portion $42_1$ of the exhaust gas sampling pipe 42 is threaded engaged with the internal threaded portion $15_2$ of the extension case 15, and the internal threaded portion $43_1$ of the cap 43 is threadedly engaged with the second external threaded portion $42_2$. A sealing member 46 comprised of a washer is clamped between the seat surface 151 of the extension case 15 and the cap 43.

The second embodiment provides effects similar to that in the first embodiment.

Although the embodiments of the present invention have been described in detail, it will be understood that the present invention is not limited to these embodiments, and various modifications in design may be made without departing from the spirit and scope of the invention defined in the claims.

What is claimed is:

1. An exhaust gas sampling device for an outboard motor comprising an engine, a body case rotatably supporting a propeller driven by said engine and which defines an exhaust gas passage for permitting an exhaust gas from said engine to be passed therethrough into water, an exhaust pipe having an exhaust port opened downwardly into said body case, an exhaust gas sampling pipe extending through said body case, and a cap for closing an outer end of the exhaust gas sampling pipe, wherein an outer wall surface of said body case opposed to said exhaust port in said exhaust pipe is provided with a seat surface, and an inner end of the exhaust gas sampling pipe, mounted to said seat surface, is loosely fitted into said exhaust port in said exhaust pipe below said engine.

* * * * *